United States Patent [19]

Sommer et al.

[11] Patent Number: 5,249,029
[45] Date of Patent: Sep. 28, 1993

[54] APPARATUS FOR DETERMINING THE SIZE DISTRIBUTION OF PIGMENT PARTICLES IN A PAINT SURFACE

[75] Inventors: Klaus Sommer, Cologne; Jürgen Thiemann, Krefeld-Bockum; Manfred Botzen, Krefeld; Detlef Riesebeck, Duisburg, all of Fed. Rep. of Germany

[73] Assignee: Bayer Aktiengesellschaft, Leverkusen, Fed. Rep. of Germany

[21] Appl. No.: 877,350

[22] Filed: Apr. 30, 1992

Related U.S. Application Data

[63] Continuation of Ser. No. 567,202, Aug. 14, 1990, abandoned.

[30] Foreign Application Priority Data

Sep. 2, 1989 [DE] Fed. Rep. of Germany ....... 3929172

[51] Int. Cl.$^5$ ............................................. G01N 15/02
[52] U.S. Cl. .................................. 356/336; 356/338; 356/237; 356/445
[58] Field of Search ...................... 356/335–343, 356/237, 445, 36, 38, 446; 250/571, 572

[56] References Cited

U.S. PATENT DOCUMENTS

| | | | |
|---|---|---|---|
| 4,377,340 | 3/1983 | Green et al. | 356/237 |
| 4,522,494 | 6/1985 | Bonner | 356/338 |
| 4,606,631 | 8/1986 | Anno et al. | 356/338 |
| 4,610,541 | 9/1986 | Tanimoto et al. | 250/572 |
| 4,636,075 | 1/1987 | Knollenberg | 356/336 |
| 4,728,190 | 3/1988 | Knollenberg | 356/336 |
| 4,893,932 | 1/1990 | Knollenberg | 356/338 |
| 4,898,471 | 2/1990 | Stonestrom et al. | 356/338 |
| 4,976,540 | 12/1990 | Kitamura et al. | 356/237 |

*Primary Examiner*—Richard A. Rosenberger
*Assistant Examiner*—Hoa Q. Pham
*Attorney, Agent, or Firm*—Sprung Horn Kramer & Woods

[57] ABSTRACT

The apparatus is based on a standard grindometer block comprising a longitudinally extending sample channel of steadily increasing depth which is filled with the paint to be investigated and then stripped and smoothed with a doctor blade. Instead of being visually evaluated, the paint surface is subjected to automatic objective evaluation in an optoelectronic apparatus comprising a light source with a focussing lens for producing a light spot on the paint surface to be investigated, a dark-field lens comprising an objective for picking up the scattered light emanating from pigment particles in the vicinity of the light spot and an aperture diaphragm for eliminating the light directly reflected at the paint surface, a photoreceiver connected to an evaluation circuit for detecting, recording and further processing the scattered light signals and a scanner for longitudinally scanning the sample channel.

8 Claims, 6 Drawing Sheets

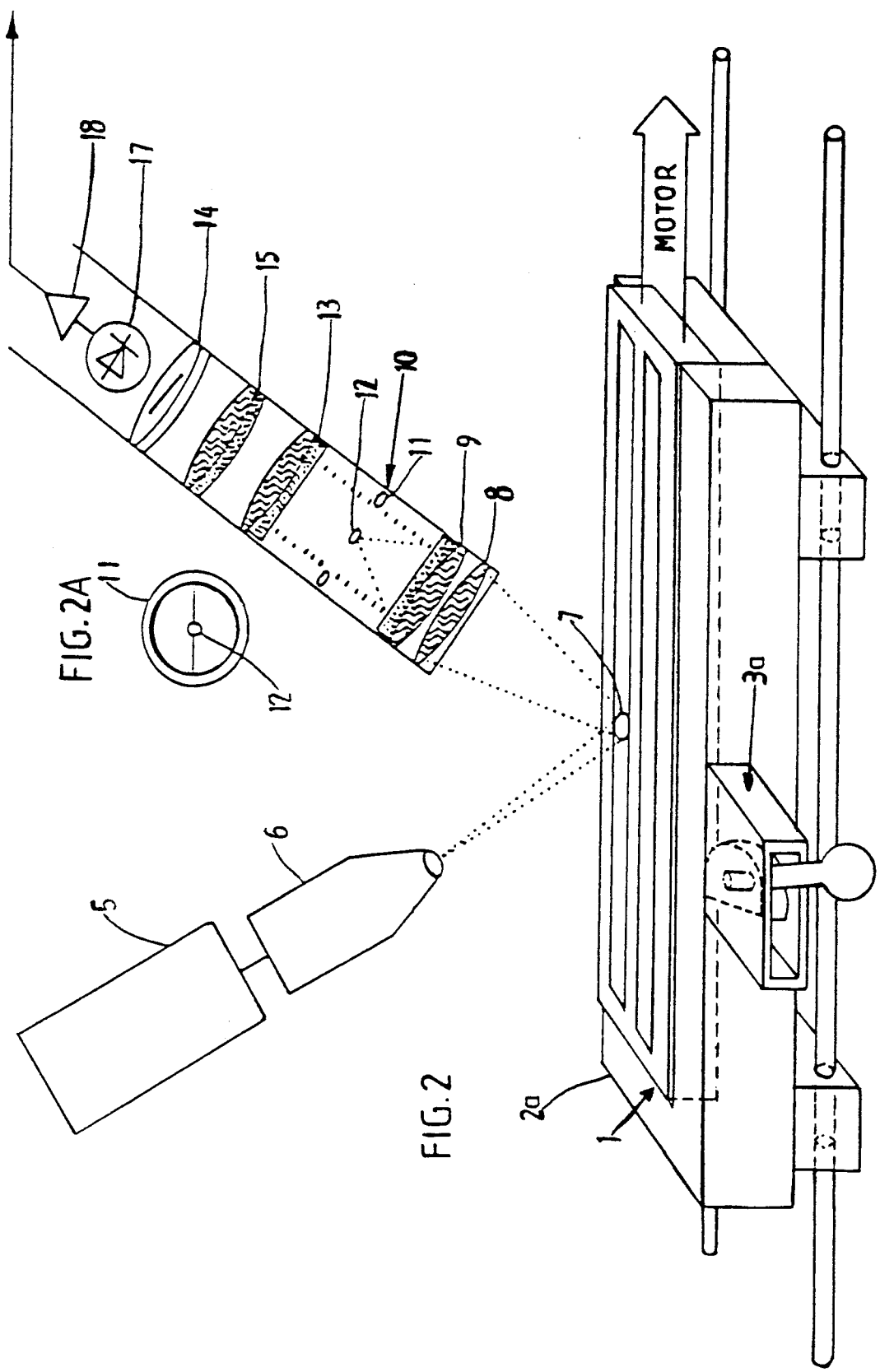

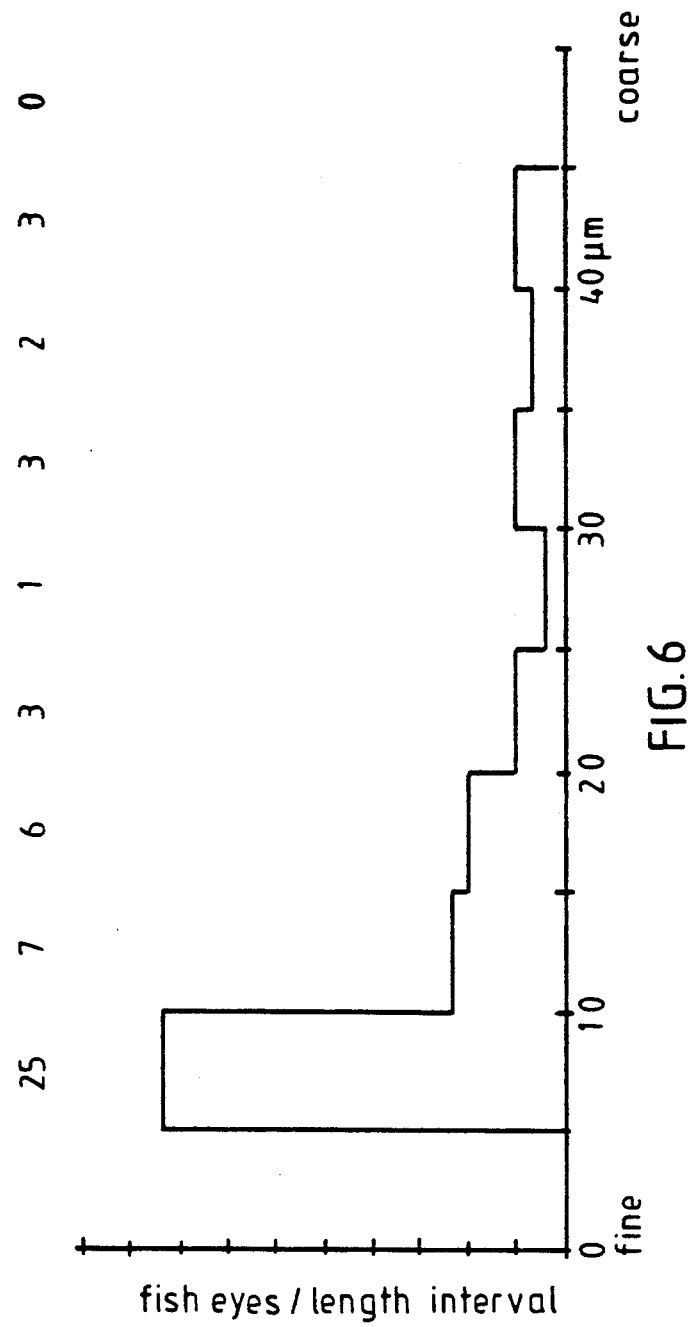

APPARATUS FOR DETERMINING THE SIZE DISTRIBUTION OF PIGMENT PARTICLES IN A PAINT SURFACE

This application is a continuation of application Ser. No. 07/567,202, filed Aug. 14, 1990, and now abandoned.

BACKGROUND OF THE INVENTION

The gloss, shade, color intensity, opacity, transparency and weathering resistance of paint coatings are influenced to a large extent by the particle size of the pigments in the paint surface.

One of the simplest and most commonly used methods of evaluating the quality of a pigment dispersion is the Hegmann test (DIN ISO1524). A so-called grindometer block is used for this test, comprising a longitudinally extending sample channel of steadily increasing depth which is filled with the paint to be investigated and then stripped and smoothed with a doctor blade (for example an Erichson grindometer with a channel length of 140 mm, a channel width of 12.5 mm and a channel depth at the deepest point of 15, 25, 50 or 100 $\mu$m). When the paint surface is stripped with the doctor blade, the pigment particles in the V-shaped channel—beginning at the point of maximum channel depth—only slip through beneath the doctor blade to that point on the grindometer block where the channel depth corresponds to the particle size. In the adjoining section where the channel depth is smaller than the particle size, the pigment particles cannot slip through beneath the edge of the doctor blade. Now, the Hegmann test mentioned above is based on visual assessment of the number and position of the pigment particles visible on the grindometer surface after stripping with the doctor blade. At the point where particle size and channel depth are equal, the pigment particles become visible at the surface. Where the channel depth is greater, the particles sink to the bottom of the channel; where the channel depth is smaller, the particles are pushed along by the doctor blade. The position read off at this point characterizes the channel depth there and hence the particle size in $\mu$m (see FIG. 1). The readings hitherto provided by the grindometer have the following further disadvantages:

the same sample is differently evaluated by different observers (subjective evaluation),
the reading is influenced by the volatility of the solvent; the time between stripping and reading should therefore be at most only 3 s,
evaluation of the pigment particles depends on the viewing angle and the light conditions.

SUMMARY OF THE INVENTION

This is where the invention comes in. It addresses the problem of developing a grindometer apparatus in which the number and position of the pigment particles is automatically determined and interpreted by a suitable evaluation system so that the grindometer readings are standardized and objective. In addition, the basic measuring process should not be affected by the color of the pigment dispersion.

Starting out from the conventional grindometer method, this problem is solved in accordance with the invention by an apparatus which embodies the following features:

a) a light source with a focussing lens for producing a light spot on the paint surface to be investigated,
b) a dark-field lens comprising an objective for measuring the scattered light emanating from pigment particles in the vicinity of the light spot and an aperture diaphragm for eliminating the light directly reflected at the paint surface,
c) a photoreceiver connected to an evaluation circuit for detecting, recording and further processing the scattered light signals and
d) a scanner for longitudinally scanning the sample channel.

The scanner advantageously consists of a synchronous motor by which the grindometer block is longitudinally displaced on a carriage linearly as a function of time, the light spot moving over the paint surface to be investigated.

In one preferred embodiment, the scattered light signals are counted in zones by the evaluation circuit along of the paint surface during scanning. To this end, a narrow slot extending perpendicularly of the sample channel is advantageously blanked out during measurement of the scattered light.

The following advantages are afforded by the invention:

application and stripping of the paint surface on the grindometer block is followed by fully automatic, objective measurement;
measurement of the particle size distribution accords very well with the conventional visual evaluation;
the reproducibility of the apparatus is sufficient for all purposes;
measurement of the particle size distribution is possible for all the usual colors.

With the optoelectronic grindometer according to the invention, it is possible for the first time to obtain detailed and uniform evaluation of the particle size distribution of pigment dispersions in any user laboratory, irrespective of the user.

One example of embodiment of the invention is described in detail in the following with reference to the accompanying drawings, wherein:

BRIEF DESCRIPTION OF THE DRAWINGS

FIGS. 2 and 2A show the basic optical structure of the apparatus.

FIG. 6 shows the number of fish eyes per length interval corresponding to the example of FIG. 5 as a function of the particle size.

DETAILED DESCRIPTION OF THE INVENTION

Figure 1:
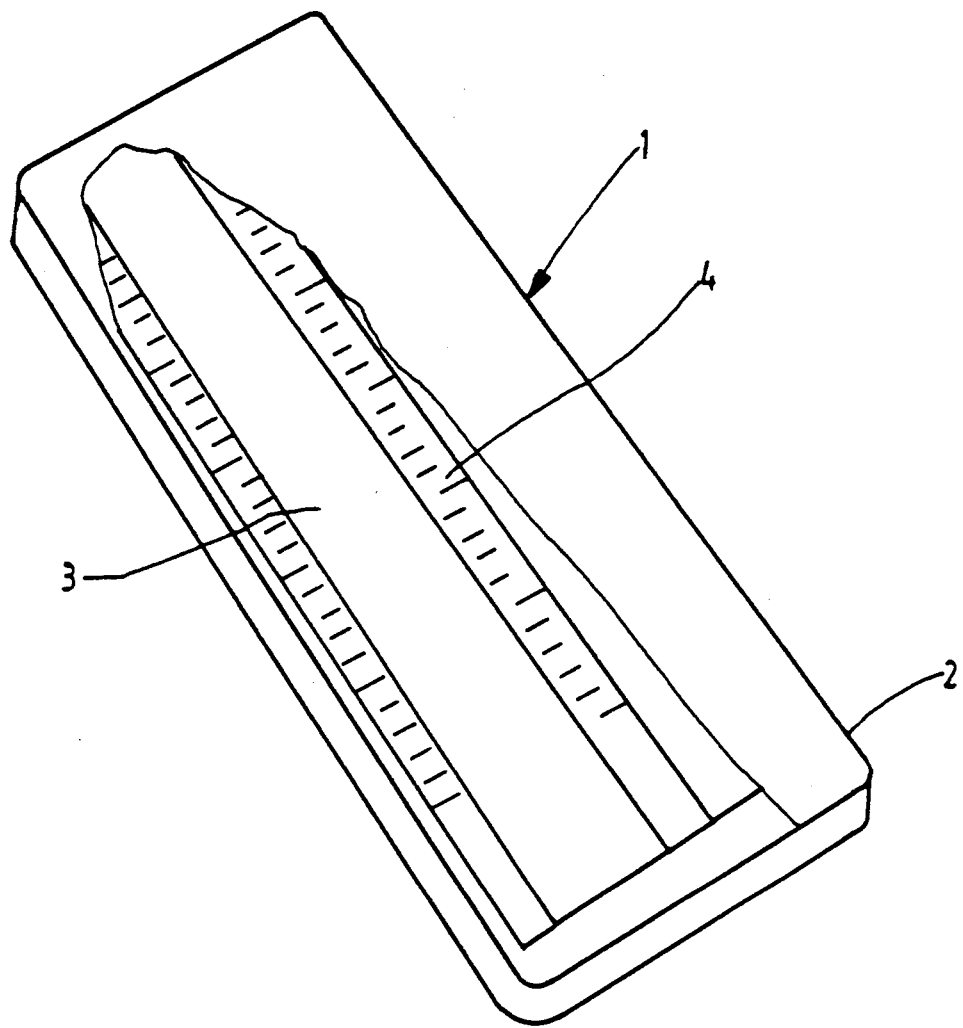
FIG. 1 shows a commercially available grindometer block.

The grindometer block shown in FIG. 1 consists of a rectangular metal plate 2 into which a V-shaped channel 3 is milled in the longitudinal direction. In this case, the channel depth shown on the scale 4 decreases linearly from the rear to the front. The width of the channel is, for example, 12.5 mm; the depth of the channel covers the range from 0 to 50 $\mu$m for example. The pigment sample to be investigated is introduced into the sample channel 3 and stripped with a doctor blade. Alternatively, a holder may also be provided which presses the doctor blade onto the grindometer block 1 under a constant force and which, at the beginning of the measurement, is situated at the outer rear end of the grindometer block.

The grindometer block 1 thus prepared is arranged according to the invention on a motor-driven carriage 2a and fixed by means of a clamping device 3a (see FIG. 2). The optical structure of the apparatus is described in the following with reference to FIG. 2. The optical configuration is adapted to the particular measurement problem of detecting individual defects in a high-gloss surface. The light beam 5 coming from a helium-neon laser is converted by a microscope objective 6 into a divergent beam so that the light spot 7 which falls onto the sample channel 3 of the grindometer block 1 illuminates the entire width of the channel. The achromates 8 and 9 focus the light directly reflected by the paint coating onto an aperture diaphragm 10 consisting of a circular ring surface 11 for defining the aperture and a central circular surface 12. FIG. 2A is a front view of elements 11 and 12. The scattered light produced by projecting pigment particles in the paint surface passes through the aperture diaphragm 10 and is projected by the lens 13 onto a 200 μm wide slot 14 while the light directly reflected at the defect-free paint surface impinges on the central part 12 of the aperture diaphragm 10 and is thus blanked out. A narrow-band interference filter 15 having a core wavelength of 633 nm is used to suppress extraneous light of other wavelengths.

Figures 3, 3A:
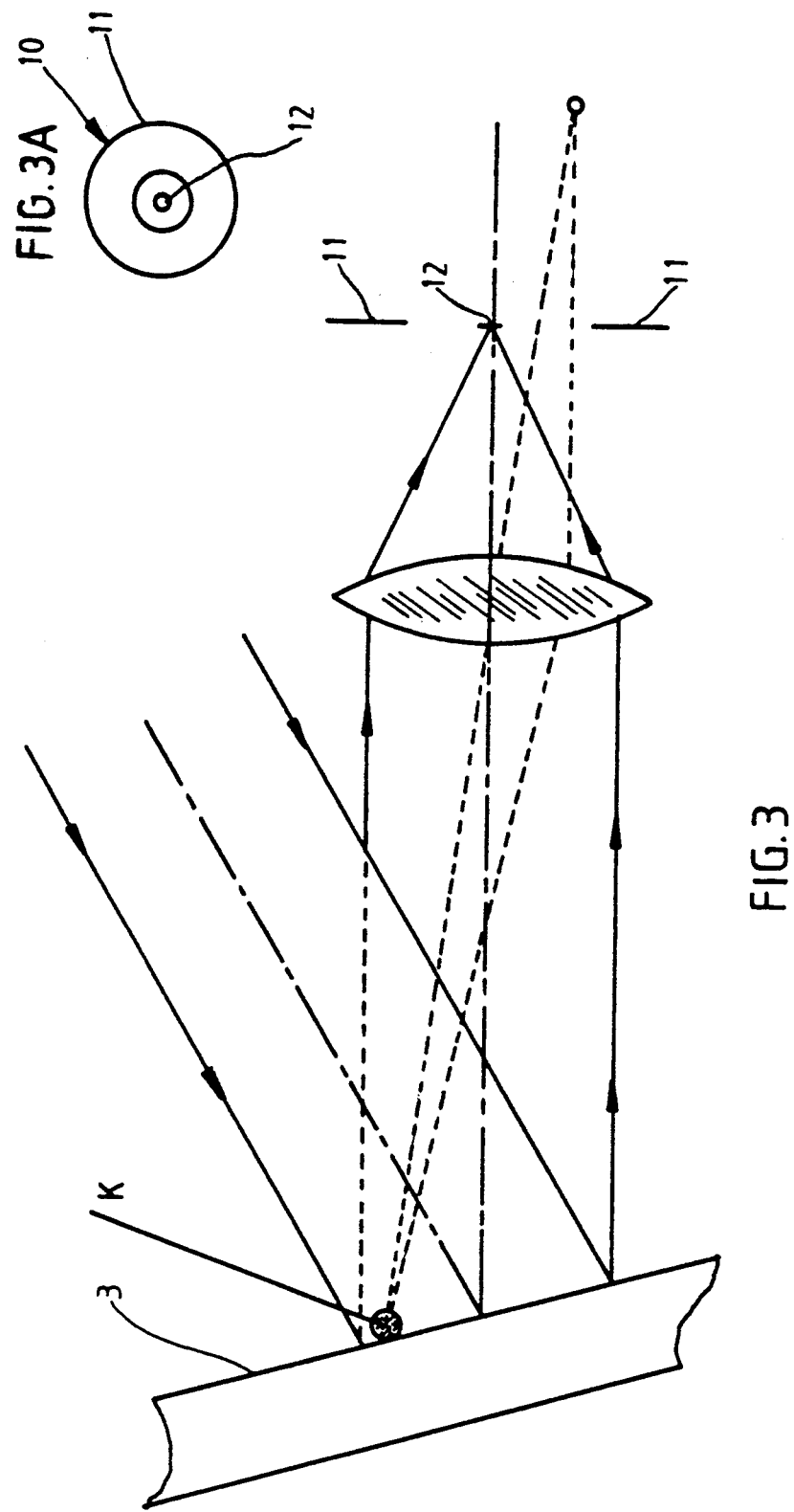
FIGS. 3 and 3A show the dark-field lens for measuring the light scattered at the pigment particles.

The effect of the aperture diaphragm 10 is based on the fact that the high-frequency and low-frequency components of the Fourier transforms of the paint surface are filtered out (spatial filtration). This is illustrated once more with reference to FIG. 3 and FIG. 3A which is a front view of elements 10–12. By virtue of the fact that the light directly reflected at the paint surface is focussed by the achromate system 8,9 onto the central part 12 of the aperture diaphragm 10 (solid-line rays) while the light scattered at a pigment particle 16 passes through the opening between the ring 11 and the central part 12 of the diaphragm, high-contrast dark-field illumination is obtained, the pigment particles 16 appearing as light spots on a dark background.

Figure 4:
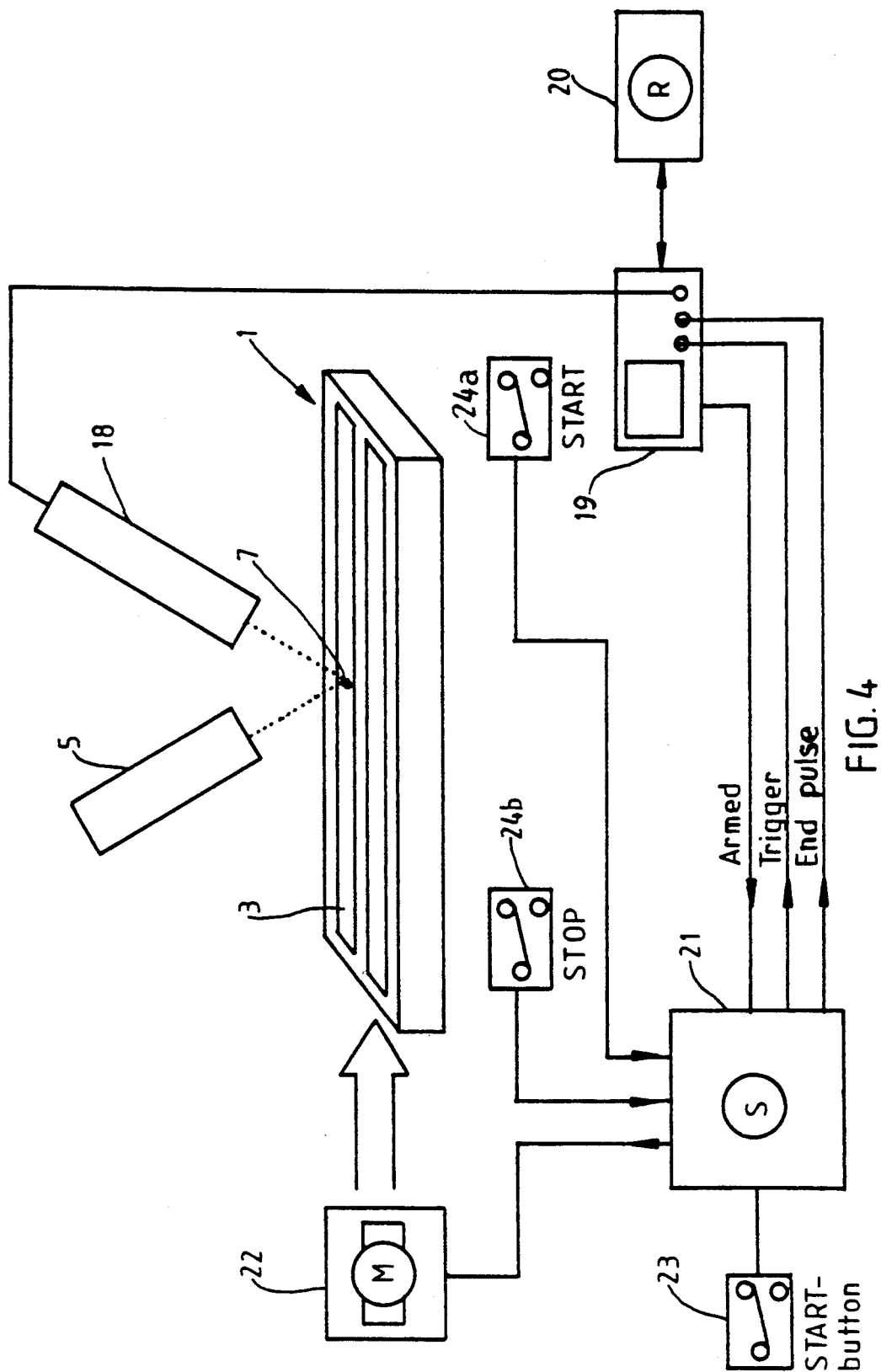
FIG. 4 shows the principle of the electronic data acquisition and interpretation.

The measuring light passing through the slot diaphragm 14 onto a silicon photodetector 17 having a surface area of 25.5×0.4 mm². The electrical signal produced is amplified by a low-drift operational amplifier 18 and then fed to a digital memory oscilloscope 19. The evaluation of the measuring signal is described in the following with reference to FIG. 4.

The electronic part of the optoelectronic grindometer consists essentially of the digital memory oscilloscope 19 linked to a computer 20 and the central control unit 21 which also controls the synchronous motor 22 for the lateral movement of the grindometer block 1.

At the beginning of a measurement, the computer 20 activates the oscilloscope 19 which, as a result of this command, passes an "ARMED" signal onto the control unit 21. Only now is the grindometer ready to start.

Actuation of the start button 23 starts up the motor drive 22 which advances the grindometer block 1 horizontally (in the arrowed direction). In the meantime, the light spot 7 scans the paint surface in the sample channel 3 (scanner 2a,5,6,7,22). The advance rate is approximately 2 cm/s. When the grindometer block 1 reaches the start mark, a start microswitch 24a activates the control unit 21 which triggers the oscilloscope 19 with a start pulse. The grindometer block 1 with the paint coating to be investigated in the sample channel 3 then advances beneath the light spot 7, the measuring signal being recorded by the oscilloscope 19.

When the grindometer block 1 finally reaches its end position, the control unit 21 is activated by a stop microswitch 24b and immediately stops the motor drive 22, interrupts the laser beam and sends an end pulse to the oscilloscope.

The data are then transferred from the oscilloscope 19 to the computer 20. The data comprise the recorded measuring signal and also the end pulse which is necessary for position resolution of the data.

Figure 5:
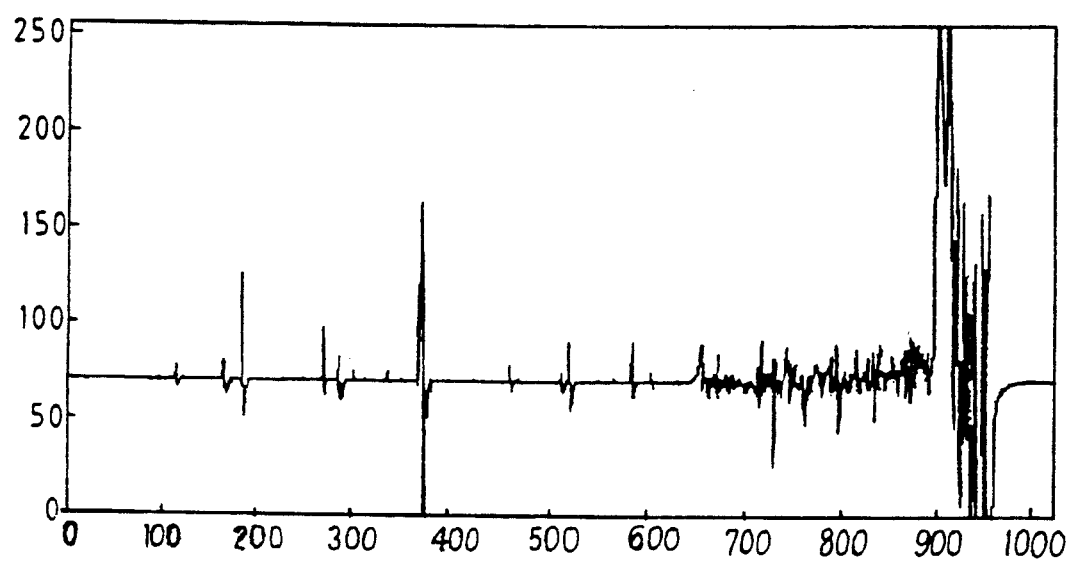
FIG. 5 shows one example of measurement for determining the number of fish eyes in a white pigment.

FIG. 5 shows a typical data record such as appears on the screen of the oscilloscope 19 after scanning of a white pigment sample in the sample channel 3 of the grindometer block 1. In this curve, the positive peaks are caused by fish eyes in the paint surface. The downwardly directed peaks remain disregarded; the middle line is taken as the base line.

FIG. 6 shows the data after computer evaluation in a histogram-like representation.

The final result obtained is the number of fish eyes found in a length interval of 5 μm (channel width) as a function of the particle size (abscissa).

We claim:

1. An apparatus for determining fineness of pigment particles in a sample of a pigmented liquid, comprising: a grindometer block comprising a longitudinally extending sample channel of steadily increasing depth receptive of a sample to be investigated and which is stripped and smoothed with a doctor blade for examination, and means for examining the stripped and smoothed sample of the block comprising a) a light source having a focusing lens for directing a light spot on the sample to be investigated,
   b) means for eliminating light directly reflected by the sample comprising an aperture diaphragm including a circular ring surface defining an aperture and a central circular surface and means for focusing light directly reflected by the sample into the aperture diaphragm at the central circular surface to block the passage of direct light through the aperture diaphragm and for directing scattered light emanating from pigment particles in the vicinity of the light spot to the aperture to permit the passage of scattered light through the aperture diaphragm,
   c) a photoreceiver for detecting the scattered light passing through said aperture diaphragm to produce scattered light signals and
   d) a scanner for longitudinally scanning the sample channel with the light spot and comprising means for longitudinally displacing the grindometer block relative to the light spot.

2. An apparatus as claimed in claim 1, wherein the means for longitudinally displacing comprises a synchronous motor for longitudinally displacing the block linearly as a function of time relative to the light spot.

3. An apparatus as claimed in claim 1, further comprising an evaluation circuit for counting the scattered light signals in zones along the sample during scanning.

4. An apparatus as claimed in claim 1, further comprising a narrow slot extending perpendicular to the sample channel and means for blanking out the narrow slot during detection of the scattered light.

5. The apparatus as claimed in claim 1, further comprising an evaluation circuit for counting the scattered light signals in zones along the sample during scanning.

6. An apparatus for determining fineness of pigment particles in a sample of a pigmented liquid, comprising: a grindometer block comprising a longitudinally extending sample channel of steadily increasing depth receptive of a sample to be investigated and which is stripped and smoothed with a doctor blade for examination, and means for examining the stripped and smoothed sample of the block comprising a) means for directing a light spot along a light path and onto the sample to be investigated to effect a scattering of light at pigment particles;

b) photoreceiving means disposed in a light path of light directly reflected from the sample for producing light signals in response to light received thereby;

c) means for blocking the light directly reflected by the sample from reaching the photoreceiving means and for directing scattered light to the photoreceiving means comprising an aperture diaphragm including a circular ring surface defining an aperture and a central circular surface and means for focusing light directly reflected by the sample into the aperture diaphragm at the central circular surface to block the passage of direct light through the aperture diaphragm and for directing scattered light emanating from pigment particles in the vicinity of the light spot to the aperture to permit the passage of scattered light through the aperture diaphragm and thereby to the photoreceiving means, whereby the photoreceiving means detects the scatted light passing through said aperture diaphragm to produce scatted light signals; and d) means for longitudinally scanning the sample channel with the light spot and comprising means for longitudinally displacing the grindometer block relative to the light spot.

7. The apparatus as claimed in claim 6, wherein the means for longitudinally displacing comprises a synchronous motor for longitudinally displacing the block linearly as a function of time relative to the light spot.

8. The apparatus as claimed in claim 6, further comprising a narrow slot extending perpendicular to the sample channel and means for blanking out the narrow slot during detection of the scattered light.

* * * * *